United States Patent
Inagaki et al.

(10) Patent No.: US 6,344,025 B1
(45) Date of Patent: Feb. 5, 2002

(54) BLOOD PRESSURE MONITOR

(75) Inventors: Takashi Inagaki; Shojiro Oku; Kentaro Mori; Mitsuru Kitamura, all of Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/494,181

(22) Filed: Jan. 31, 2000

(30) Foreign Application Priority Data

Feb. 19, 1999 (JP) ............................................ 11-041109

(51) Int. Cl.[7] ................................................. A61B 5/00
(52) U.S. Cl. ........................ 600/490; 600/494; 600/500; 600/485; 600/499
(58) Field of Search ................................. 600/485, 490, 600/493–6, 500, 499

(56) References Cited

U.S. PATENT DOCUMENTS

| | | | | |
|---|---|---|---|---|
| 3,557,779 A | * | 1/1971 | Weinstein | 600/496 |
| 4,248,242 A | * | 2/1981 | Tamm | 600/494 |
| 4,459,991 A | * | 7/1984 | Hatschek | 600/494 |
| 4,549,550 A | * | 10/1985 | Kami | 600/499 |
| 5,335,665 A | * | 8/1994 | Suzuki | 600/493 |
| 5,687,732 A | * | 11/1997 | Inagaki et al. | 600/490 |

* cited by examiner

*Primary Examiner*—Robert L. Nasser, Jr.
(74) *Attorney, Agent, or Firm*—Morrison & Foerster, LLP

(57) ABSTRACT

A blood pressure monitor includes a cuff to be worn on a living body portion provided with an air component for inflating and deflating said cuff, and a main body detachably mounted on the cuff provided with an electrical component, in which the main body is electrically connected with the cuff by wire or wireless.

9 Claims, 19 Drawing Sheets

BLOOD PRESSURE MONITOR

BACKGROUND OF THE INVENTION

1. Field of the Invention

This invention relates to an a blood pressure monitor detecting a pulse wave from a living body portion such as a wrist or an arm of a human body to measure a blood pressure, and more particularly to an improved blood pressure monitor of which main body is detachably mounted on a cuff to be worn on the wrist or the arm.

2. Description of the Related Art

There is well known a blood pressure monitors wherein a cuff worn on a living body portion such as a wrist or an arm of a person is united with a main body of the monitor as a single unit. A first conventional blood pressure monitor is so constructed that a main body is secured to a cuff by a screw or a hook.

A second conventional blood pressure monitor is so constructed that a main body is adapted to be detachably mounted on a cuff but the main body is connected with the cuff by an air tube as shown in FIG. 19. In FIG. 19 at (a) pad fasteners 91 and 94 are respectively disposed on a cuff 90 and a main body 93 which are connected each other by an air tube 97. In FIG. 19 at (b) a hook 92 protrudes from a cuff 90 and a hook engagement opening 95 is disposed on a main body 93, and the cuff 90 and the body 93 are connected by an air tube 97. These second conventional monitors allow the main body 93 to be detachably mounted on the cuff 90 worn on the living body portion. Each main body 93 is provided with another air tube 98 connected with a manual pump (not shown in drawings) or an electric pump instead of the manual pump to inflate the cuff 90.

The first conventional blood pressure monitor does not allow the main body to be detached from the cuff, thereby causing disadvantages such that it is hard for a person of presbyopia to view a display disposed on the main body, to manipulate an operation portion such as a power switch and to operate the monitor when the cuff is worn on the arm.

As the second conventional blood pressure monitor of FIG. 19 is used by detaching the main body 93 from the cuff 90, it can resolve such hard view of the display and hard manipulation of the operation portion by the person of presbyopia. When the main body 93 is mounted on the cuff 93 as a single unit for its use, however, the cuff 90 and the main body 93 are connected by comparatively big and long air tube 97, and the excess air tube 97 disturbs the operation of the monitor and deforms its appearance. The second conventional monitor employing the pad fasteners 91 and 94 of FIG. 19 at (a) cannot ensure strongly holding the main body 93 by the cuff 90, thereby resulting in a risk such that the main body 93 is detached from the cuff 90 and drops during operation.

SUMMARY OF THE INVENTION

It is, therefore, a primary object of this invention to provide a blood pressure monitor having improved visualization and manipulation without deteriorating the simplicity and portability of a single unification of a cuff and a main body.

According to one aspect of this invention, there is provided a blood pressure monitor including a cuff to be worn on a living body portion provided with an air component for inflating and deflating the cuff, and a main body detachably mounted on the cuff provided with an electrical component, the main body being electrically connected with the cuff by wire or wireless.

This blood pressure monitor is different from the above-described second conventional blood pressure monitor. This cuff is installed by the air component such as an electric pump, an exhaust valve, a tube and so forth, and this main body is installed by only the electrical component such as a display, an operation unit and so forth, so that the main body is not necessary to be connected with the cuff by an air tube and the body and cuff are electrically connected by wire or wireless.

When they are connected by wire, a narrow and easy use cable may be employed in comparison with an air tube, thereby improving the operation when the main body is detached from the cuff for use. When the cuff and the main body are coupled as a single unit, there may be employed a reel mechanism for winding the wire or a wire removing mechanism, thereby avoiding the disturbance by the wire during operation.

When wireless is employed for the electric connection between the cuff and the main body, there is no component therebetween and the operability is further improved. Thus, the visualization and the manipulation may be improved.

According to another aspect of this invention, there is provided a blood pressure monitor including a cuff to be worn on a living body portion, a main body detachably mounted on the cuff provided with an air component for inflating and deflating the cuff, and air connection openings respectively disposed on the cuff and the main body which are adapted to be directly connected each other when the main body is mounted on the cuff but indirectly connected through an air tube when the main body is detached from the cuff. According to this blood pressure monitor, both air connection openings are directly connected each other when the main body and the cuff are coupled as a single unit for measurement, but indirectly connected through the air tube when the main body is detached for measurement, thereby improving its usefulness of the visualization and the manipulation as well as the usefulness of the foregoing blood pressure monitor of this invention.

BRIEF DESCRIPTION OF THE DRAWINGS

Other objectives and advantages of this invention will be more readily apparent from the following detailed description provided in conjunction with the following figures, of which.

DETAILED DESCRIPTION OF THE PREFERRED EMBODIMENTS

Figure 1:
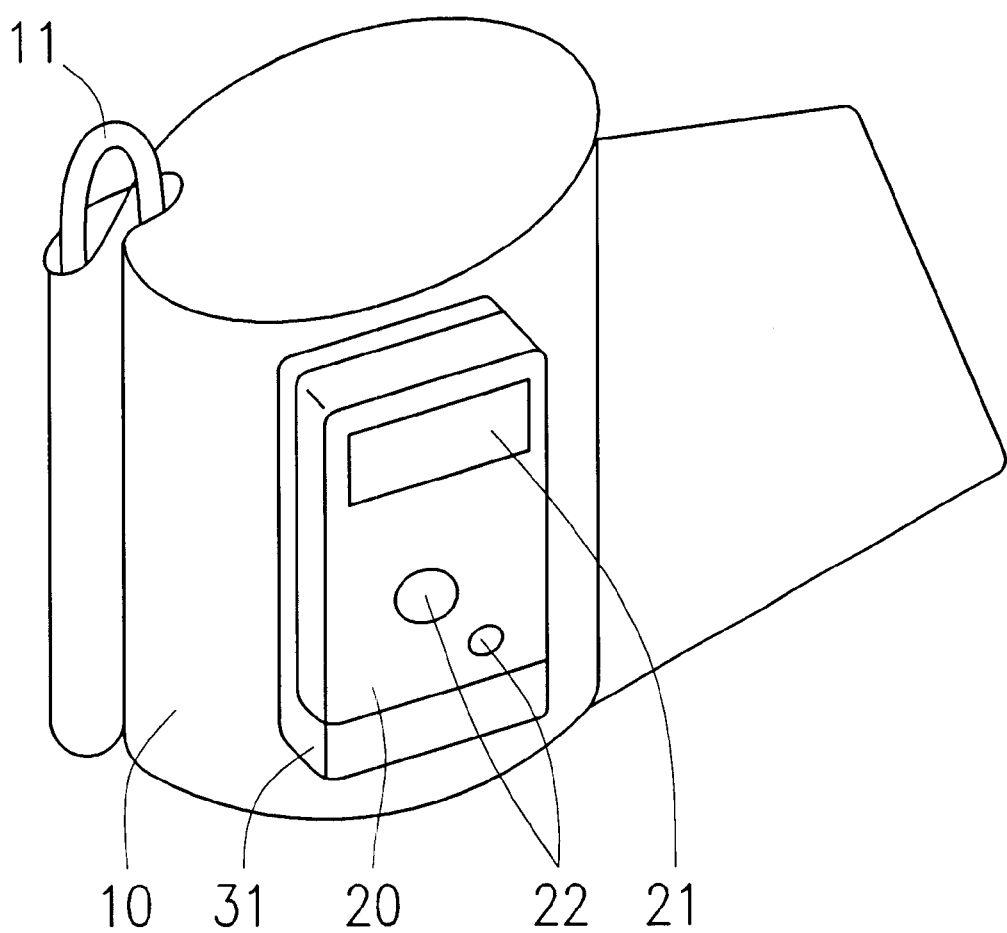
FIG. 1 is a perspective view of a blood pressure monitor in a single unit state wherein a cuff and a main body are united as a first embodiment of this invention.
Figure 2:
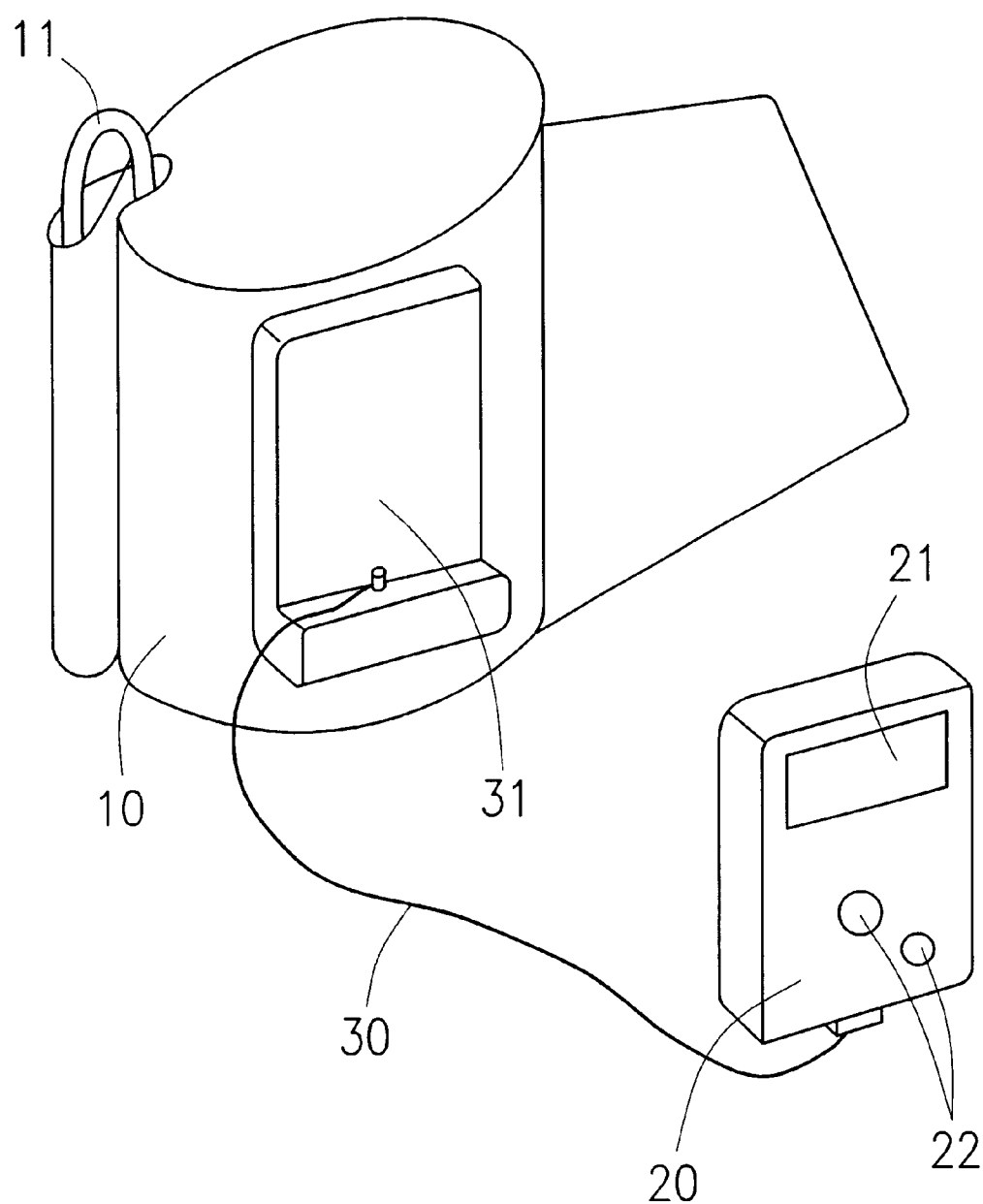
FIG. 2 is a perspective view of the blood pressure monitor of FIG. 1 in a detached state wherein the main body is detached from the cuff.

Referring, now, to FIG. 1, there is a perspective view of a blood pressure monitor in a single unit state according to a first embodiment of this invention, and in FIG. 2 there is shown the blood pressure monitor of FIG. 1 in a detached state. The blood pressure monitor of this first embodiment includes a cuff 10 to be wound around and worn on a living body portion such as a wrist or an arm of a human body, and a main body 20 provided with a display 21 and a manipulation portion (a power switch and so forth) to be detachably mounted on the cuff 10, wherein the cuff 10 is electrically connected with the main body 20 by an electric wire or cord. The cuff 10 is provided with a metal piece to be turned around for adjusting the length to be wound around the living body portion, and encloses an air bag therewithin. The cuff 10 at a main body mounting portion is provided with a base 31 to be detachably mounted by the main body 20. The base 31 includes an air component such as an electric pump, an exhaust valve, a tube and so forth for inflating and deflating the cuff. On the other hand, the main body 20 includes an electric component such as a display 21, a manipulation portion 22 and so forth.

Any particular installation of the body 20 to the base 31 is not shown in FIG. 2, but, for example, it is performed by the engagement of a concave portion and a convex portion. The cord 30 may be adjusted to a proper length by employing a take-up mechanism disposed on the base 31 or the body 20, or detachably connected with the cuff 10 and the body 20 by a connector. If the cord 30 is designed to be detachably connected, for instance, each code connecting portion of the base 31 and the body 20 is provided with a connector to electrically connect the cuff 10 with the body 20.

When this blood pressure monitor is used in the single unit state of FIG. 1 in which the main body 20 is mounted on the cuff 10 worn on the living body portion, the cord 30 is adjusted to a proper length by wound by the above-described take-up mechanism, or may be removed. In this embodiment there is not employed any air tube for connection between the cuff 10 and the main body 20, the inconvenience by the tube may be avoided and the cord 30 does not disturb use of the blood pressure monitor in the single unite state. The cuff 10 and the main body 20 are united as a single, resulting in easy and handy use.

On the other hand, when this blood pressure monitor is used in the detached state of FIG. 2 in which the main body 20 is separated from the cuff 10, the cord 30 is pulled out from the take-up mechanism to be adjusted to a proper length or connected between the base 31 and the main body 20. In this detached state the main body 20 may be located on any suitable position when a person of presbyopia measures the person's blood pressure by oneself or when other person measures a patient on a bed, thereby improving the visualization of the display 21 and the operability of the manipulation portion 22 of the main body 20, resulting in handy and easy use. Moreover, the cord 30 having a smaller diameter than that of any air tube and good degrees of freedom is employed to connect the main body 20 with the cuff 10, thereby allowing the main body 20 to be located at any desired position with a relatively free degree.

Figure 3:
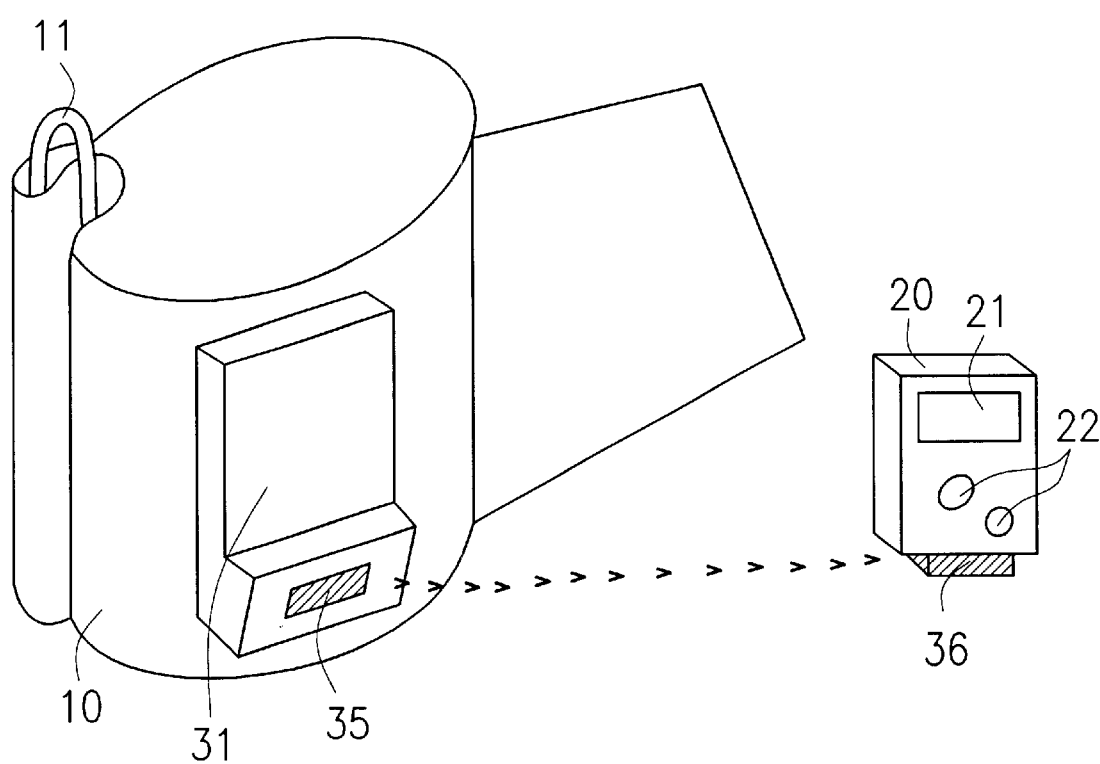
FIG. 3 is a perspective view of a blood pressure monitor in a detached state wherein the a body is detached from a cuff as a second embodiment.

In FIG. 3 there is shown a blood pressure monitor as a second embodiment of this invention. The parts corresponding to those in the blood pressure monitor of the first embodiment are given the same reference symbols. In the blood pressure monitor of this embodiment a main body 20 is electrically connected with a cuff 10 by wireless such as an infrared wireless. The base 31 of the cuff 10 and the main body 20 are respectively provided with transmission and reception portions 35 and 36 to mutually communicate operation signals and measured signals.

There is not any physical component for connection between the cuff 10 and the main body 20, thereby providing very convenient use when the cuff 10 and the main body 20 are used as a coupled single unit or detached units. Besides, when the cuff 10 remains to be worn on the wrist or the arm, the main body 20 may be detached from the cuff 10, whereby the cuff 10 does not become heavy and the arm is not tired, and seems to be a decoration band with the improvement of appearance.

Figure 4:
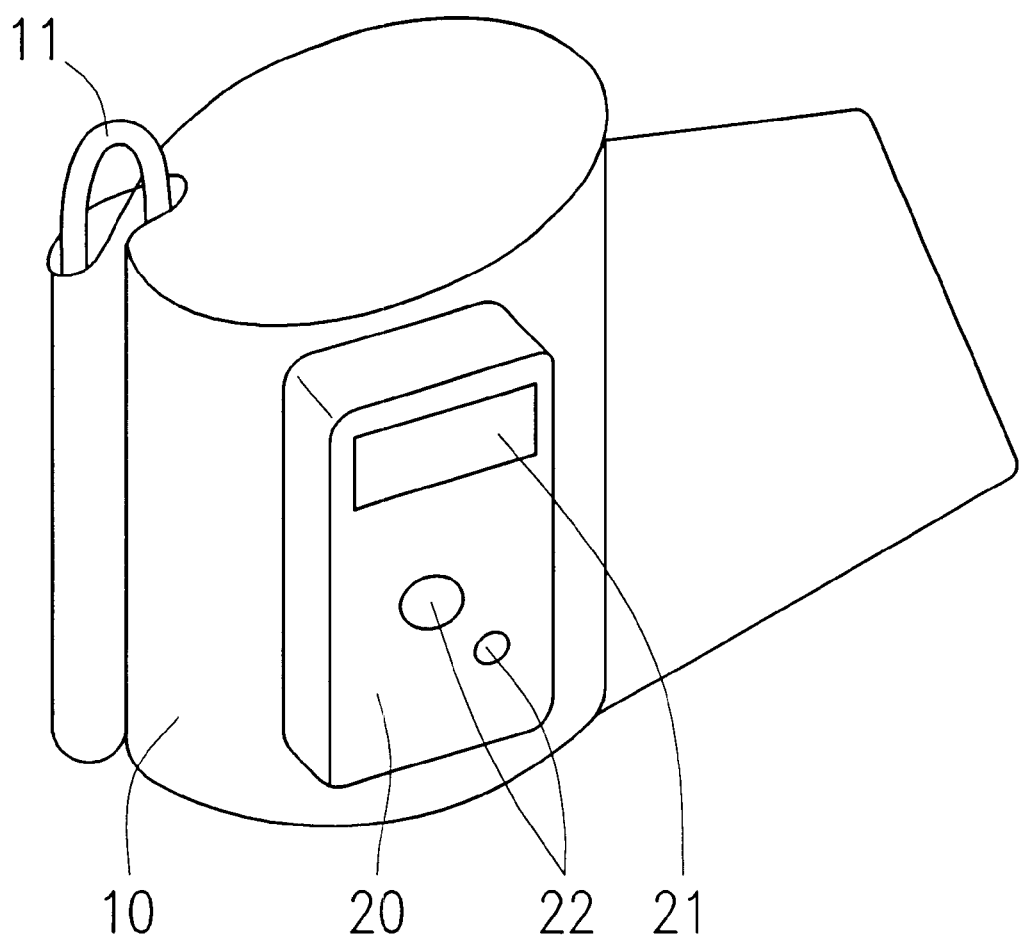
FIG. 4 is a perspective view of a blood pressure monitor in a single unit state wherein a cuff and a main body are united as a third embodiment of this invention.
Figure 5:
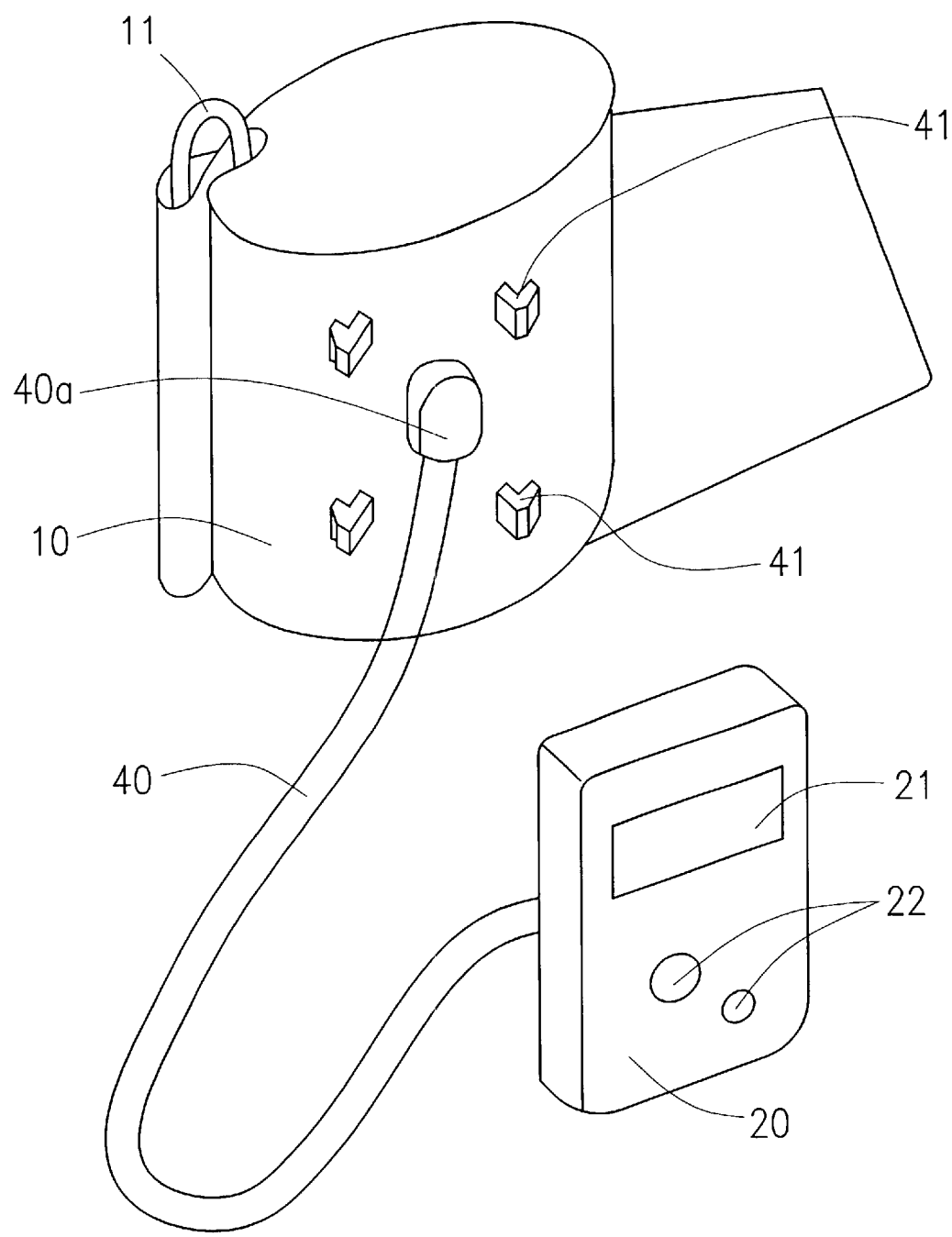
FIG. 5 is a perspective view of the blood pressure monitor of FIG. 4 in a detached state wherein the main body is detached from the cuff.

In FIG. 4 there is shown a perspective view of a blood pressure monitor in a single unit state wherein a cuff 10 and a main body 20 are coupled as a third embodiment of this invention, and in FIG. 5 there is a perspective view of the blood pressure monitor in a detached state wherein the main body 20 is detached from the cuff 10. The main body 20 includes an air component, and an air tube 40 is employed when the cuff and the main body are used in the detached state. Four hooks (projections) 41 are disposed on a main body mounting portion of the cuff 10, and four engagement openings (projection receiving portions, not shown) are disposed on a rear wall of the main body 20, wherein the main body 20 may be mounted on the cuff 10 by engagement between the hooks 41 and the engagement openings. The number of the hooks 41 may be changed to a desired number and their location may be changed if desired.

Air connection mouths (not shown) are disposed on the main body mounting portion of the cuff 10 and the rear wall of the main body 20 so that they may be directly connected each other when the main body 20 is mounted on the cuff 10 or be connected by the air tube 40. Connectors 40a and 40b as shown in FIG. 7 are disposed on both ends of the tube 40 so that the air tube 40 may be easily and airtightly connected or disconnected.

When the cuff 10 and the main body 20 are used as the single coupled unit as shown in FIG. 4, the air tube is removed. Since both air connection mouths come into direct contact each other, there is not a hindrance in entrance and exit of air between cuff 10 and body 20.

When the cuff 10 and the body 20 are used in detached state as shown in FIG. 5, the hooks 41 of the cuff 10 are removed from the engagement openings of the main body 20 and the connectors 40a and 40b of the air tube 40 are connected with the both air connection mouths.

Figure 6:
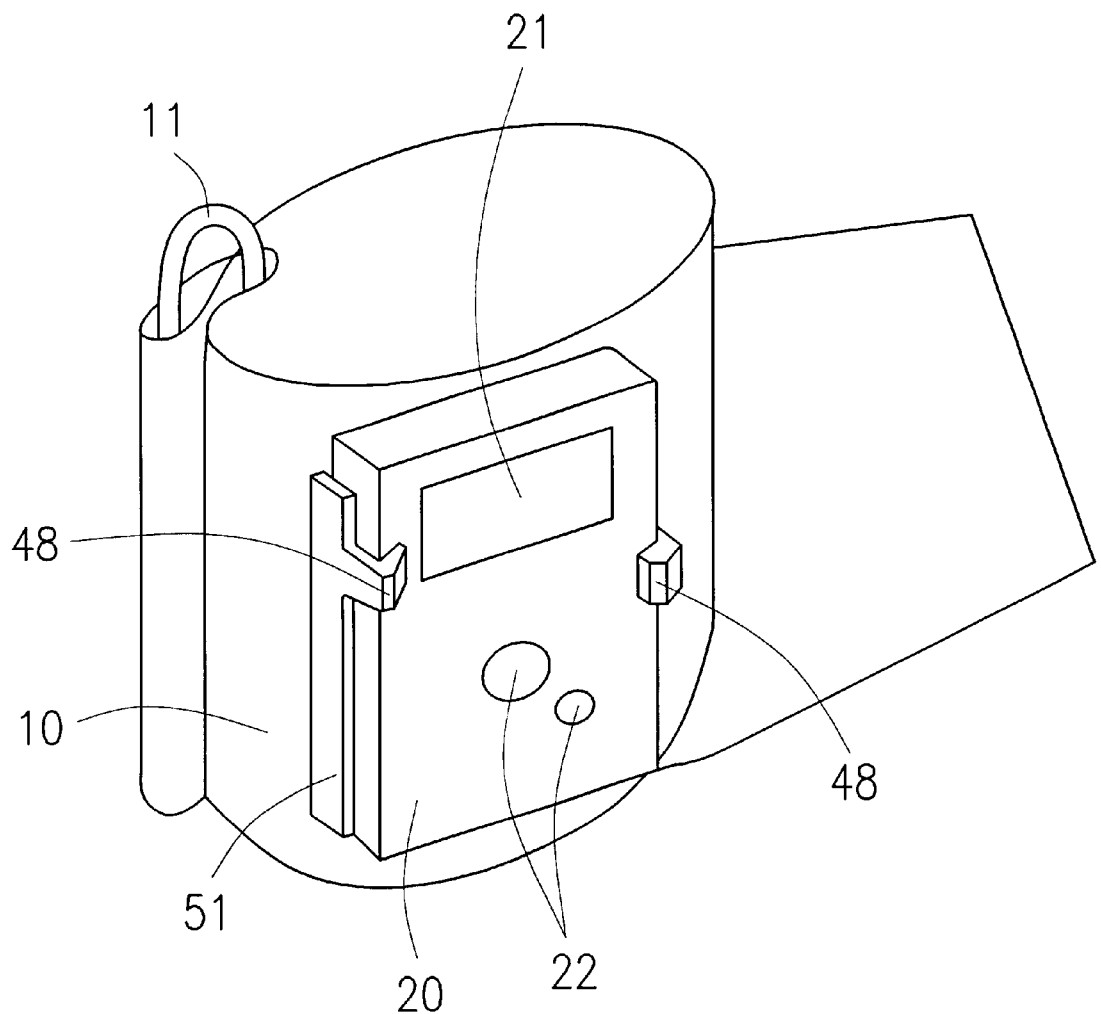
FIG. 6 is a perspective view of a blood pressure monitor in a single unit state wherein a cuff and a main body are united as a fourth embodiment of this invention.
Figure 7:
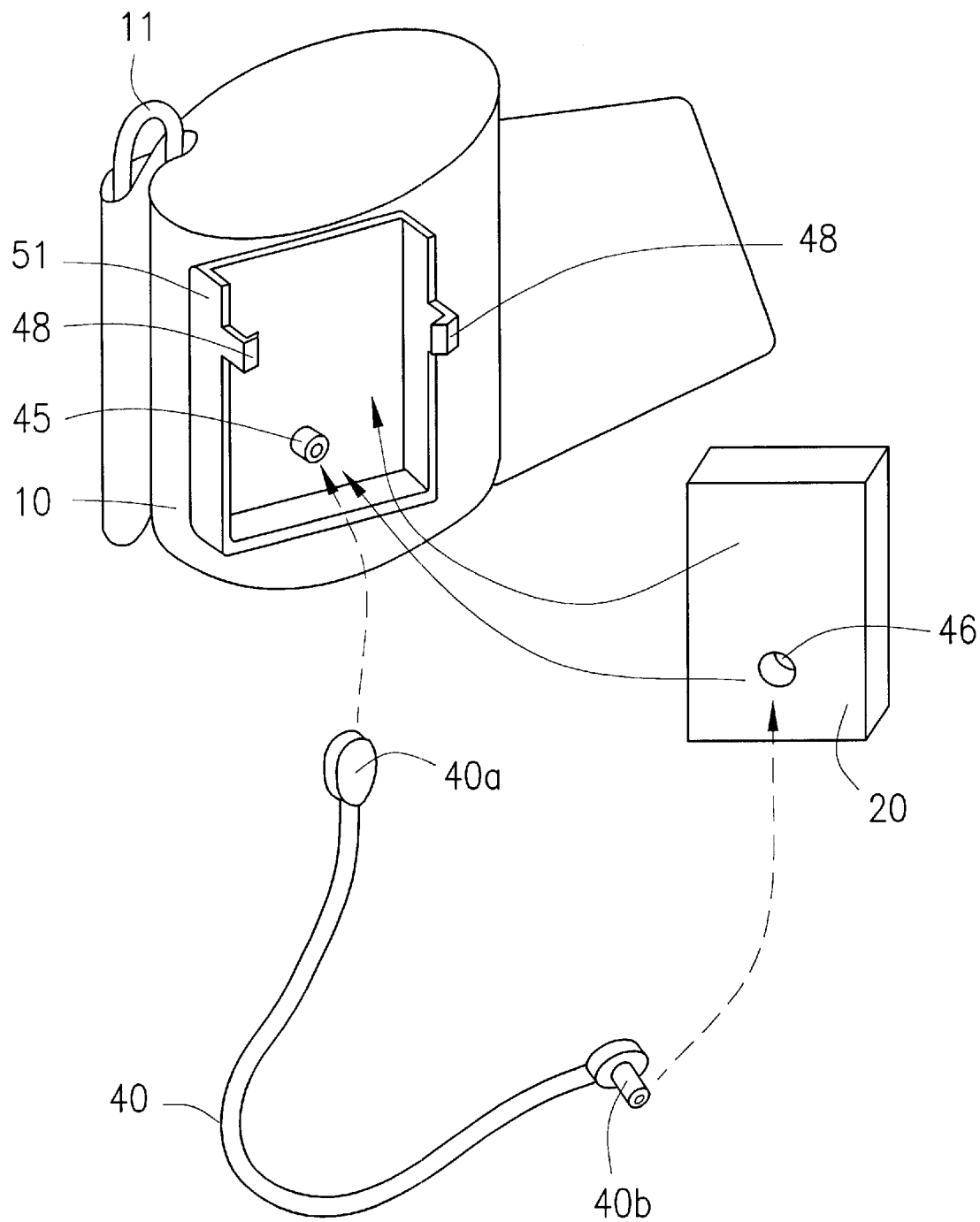
FIG. 7 is a perspective view of the blood pressure monitor of FIG. 6 in a detached state wherein the main body is detached from the cuff.

In FIG. 6 there is shown a blood pressure monitor in a single unit state wherein a cuff 10 and a main body 20 are coupled as a fourth embodiment of this invention, and in FIG. 7 there is a detached view of the blood pressure monitor in a detached state wherein the main body 20 is detached from the cuff 10. As for this blood pressure monitor, a base 51 of the configuration shown in FIG. 7 is established in a body mounting portion of the cuff 10, and provided with an air connection mouth 45 and a pair of hooks (projections) 48. An air connection mouth 46 is disposed on a rear wall of the main body 20. As the hooks 48 come into engagement with the main body 20, the main body 20 is supported by the base 51. The air tube 40 for connecting both air connection mouths 45 and 46 is provided with connectors 40a and 40b on both ends of the tube 40, and easily and airtightly connected with the air connection mouths 45 and 46 by inserting the connectors 40a and 40b into the air connection mouths 45 and 46.

When the cuff 10 and the main body 20 are used as a coupled single unit as shown in FIG. 6, the air tube 40 is detached and the main body 20 is mounted on the base 51, wherein both air connection mouths 45 and 46 are directly connected each other. When the cuff and the body are used in the detached state as shown in FIG. 7, the main body 20 is detached from the base 51, and the air tube 40 is connected with the air connection mouths 45 and 46.

Figure 8:
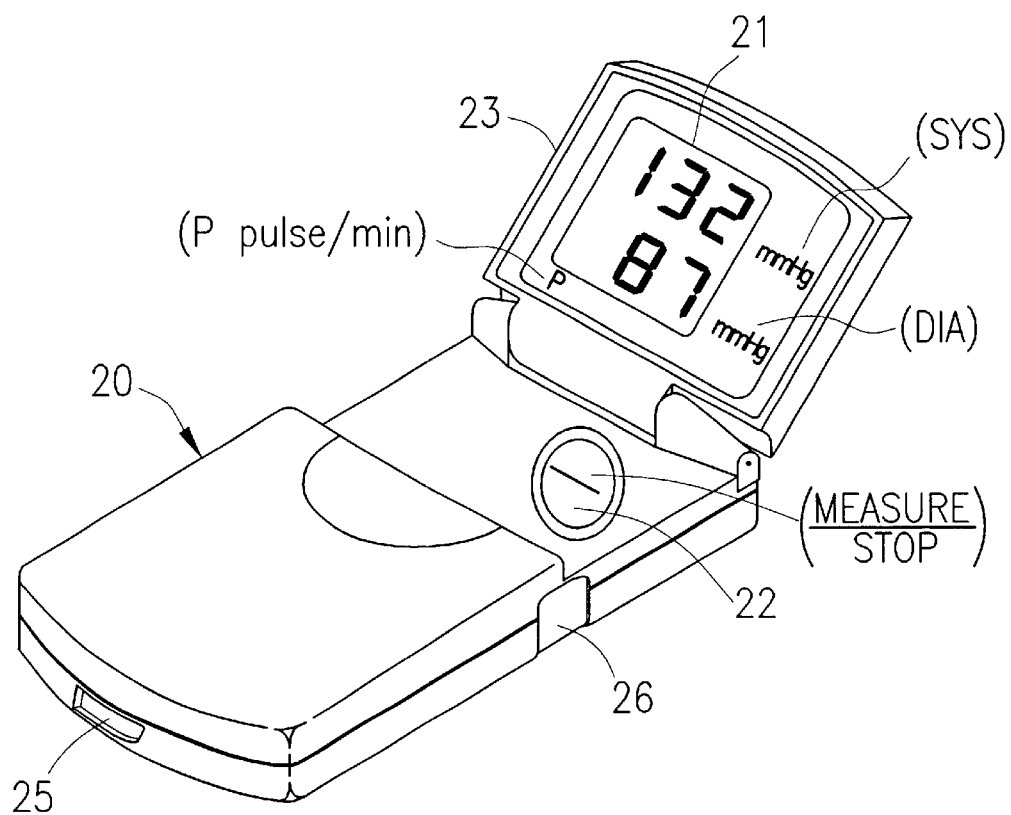
FIG. 8 is a perspective view of a main body of a blood pressure monitor as a fifth embodiment of this invention.
Figure 9A:
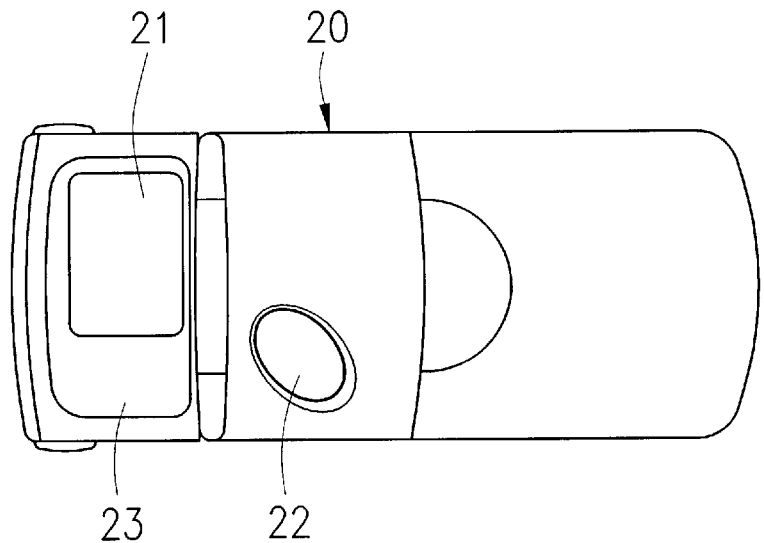
FIG. 9 at (a) shows a top view of the main body of FIG. 8, and at (b) shows a bottom view of the same.
Figure 9B:
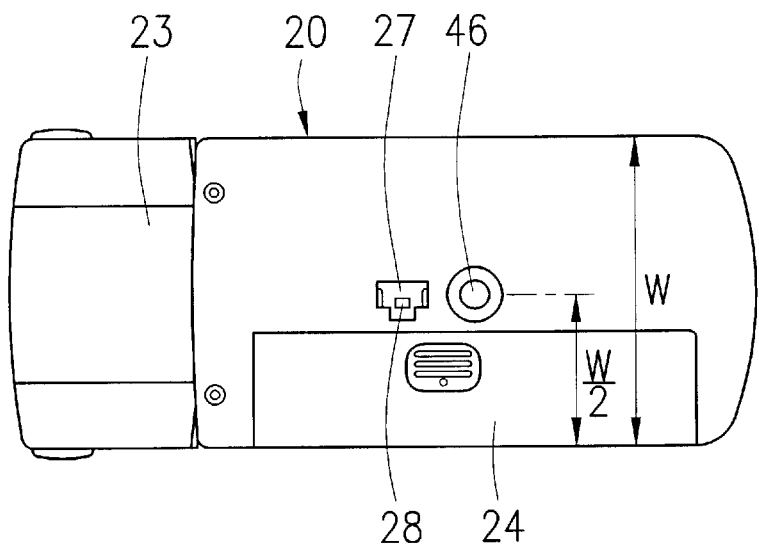
Figure 10:
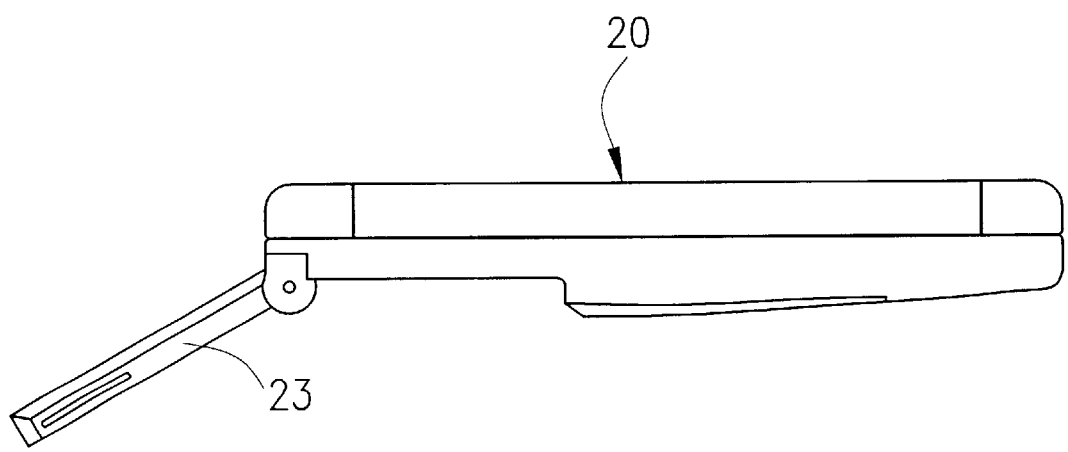
FIG. 10 shows a side view of the main body of FIG. 9 at (b)

In FIG. 8 there is shown a perspective view of a main body 20 of a blood pressure monitor as a fifth embodiment of this invention. FIG. 9 at (a) shows a top view of the main body 20, and at (b) shows a bottom view of the same. FIG. 10 shows a side view of the main body 20 of FIG. 9 at (b). The main body 20 is provided with a display cover 23 in an open-and-close relationship. A display 21 is disposed on an inner wall of the display cover 23 that stands as it is used. A battery cover 24 is detachably mounted on a reversal wall of the main body 20.

The main body 20 on its one side in a width direction thereof is provided with a groove (engagement receiving portion) 25, and on its other side in a longitudinal direction is provided with a push button 26 movable in the width direction. The pushbutton 26 is always applied by accompanying force from a coil spring so as to protrude from the other one side of the body 20, and may be depressed against the accompanying force. An opening 27 is disposed on a bottom wall of the body 20, and a nail (projection) 28 is fixed within the opening 27. The nail 28 is formed with the button 26 as a single unit, and designed to be slightly displaced in a moving direction of the button 26 as it is depressed.

An air connection mouth 46 disposed on the bottom wall of the main body 20 includes O-ring on its circumference face peripheral, but the O-ring somewhat protrudes from the circumference face. The air connection mouth 46 of this embodiment is positioned about a center of the main body 20 in a longitudinal direction of a cuff 10 shown in FIG. 11 when the main body 20 is mounted on the cuff 10 (viz. in a width direction of the main body 20). That is, in FIG. 9 at (b), the air connection mouth 46 is disposed at a position of W/2 wherein "W" is a dimension of the main body 20 in its width direction.

Figure 11:
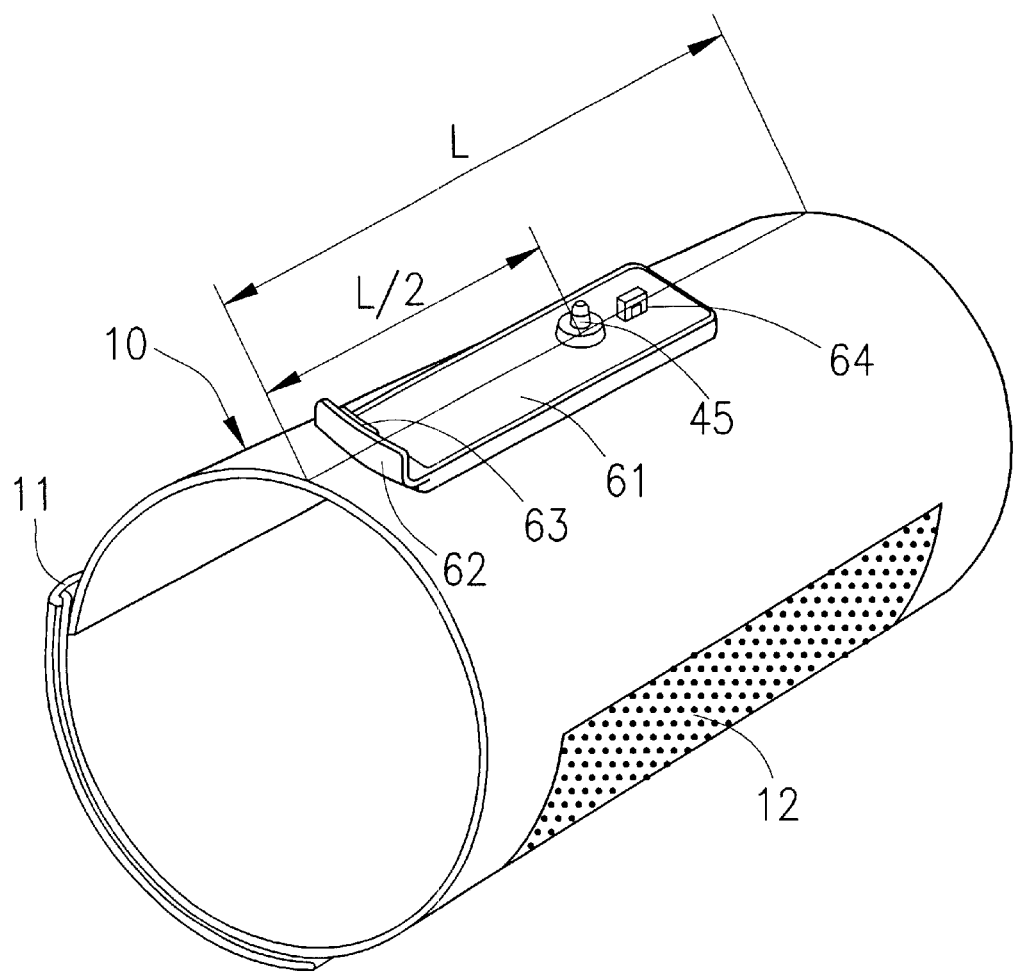
FIG. 11 is a perspective view of a cuff to be mounted by the main body of FIG. 8.

In FIG. 11 there is shown a perspective view of the cuff 10. A base 61 is secured to the cuff 10 at its main body mounting portion to be detachably mounted by the main body 20. The base 61 is provided with a convex portion (engagement portion) 63 disposed on a wall 62 on one end side of the base 61 to be detachably engaged with the groove 25 of the main body 20, an air connection mouth 45 corresponding to the air connection mouth 46 of the main body 20, and a nail receiving portion (projection receiving portion) 64 to be detachably engaged with the nail 28. The air connection mouth 45 of this embodiment is positioned about a center of the cuff 10 in a width direction of the cuff 10. That is, the air connection mouth 45 is disposed at a position of "L/2" wherein "L" is a dimension of the cuff 10 in its width direction. A pad fastener 12 is disposed on an appropriate portion of a surface of the cuff 10.

Figure 12A:
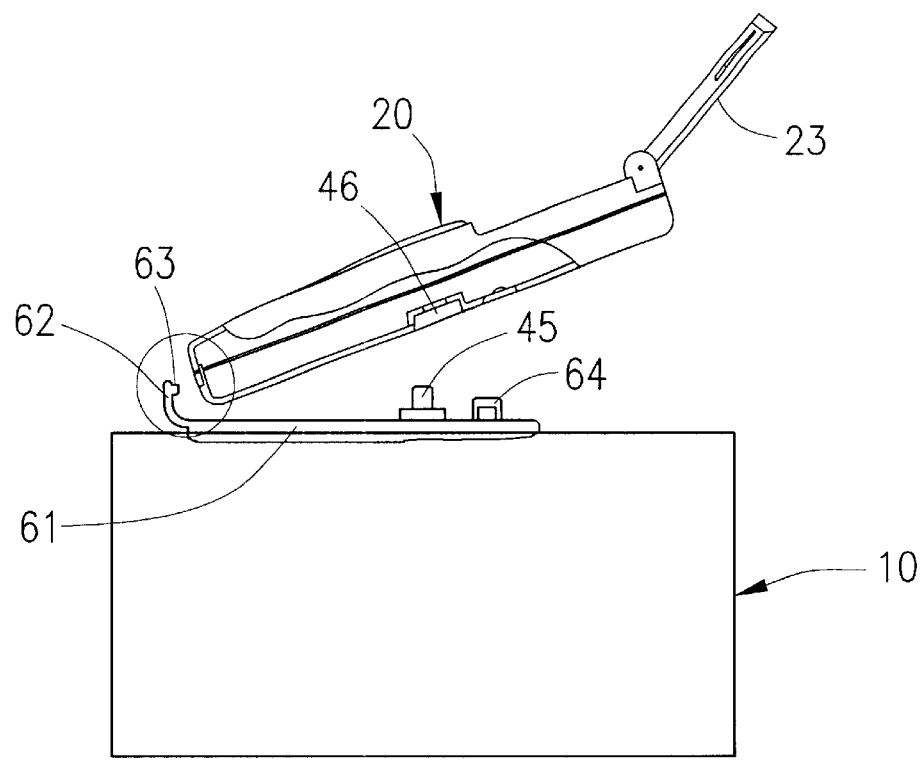
FIG. 12 shows at (a) a partially broken side view of the main body of FIG. 8 and the cuff of FIG. 11 to illustrate a mounting method for mounting the main body on the cuff of FIG. 11, and at (b) an enlargement view of a circled portion of FIG. 12 at (a)
Figure 12B:
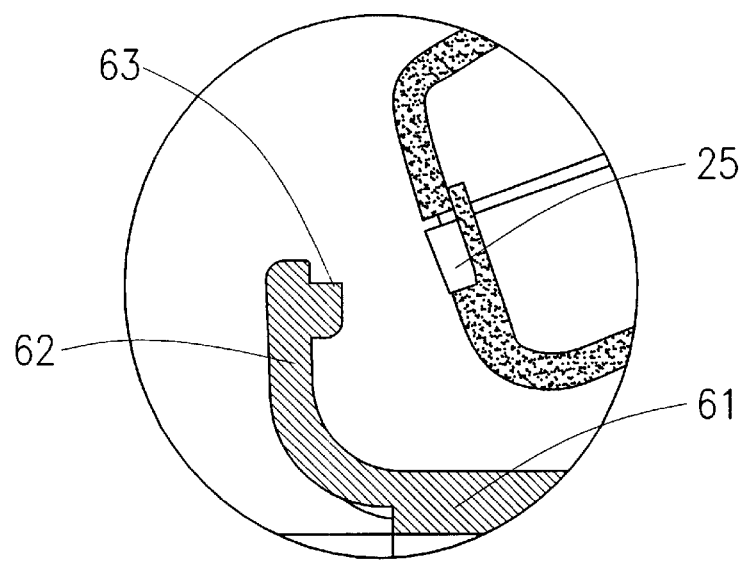
Figure 13A:
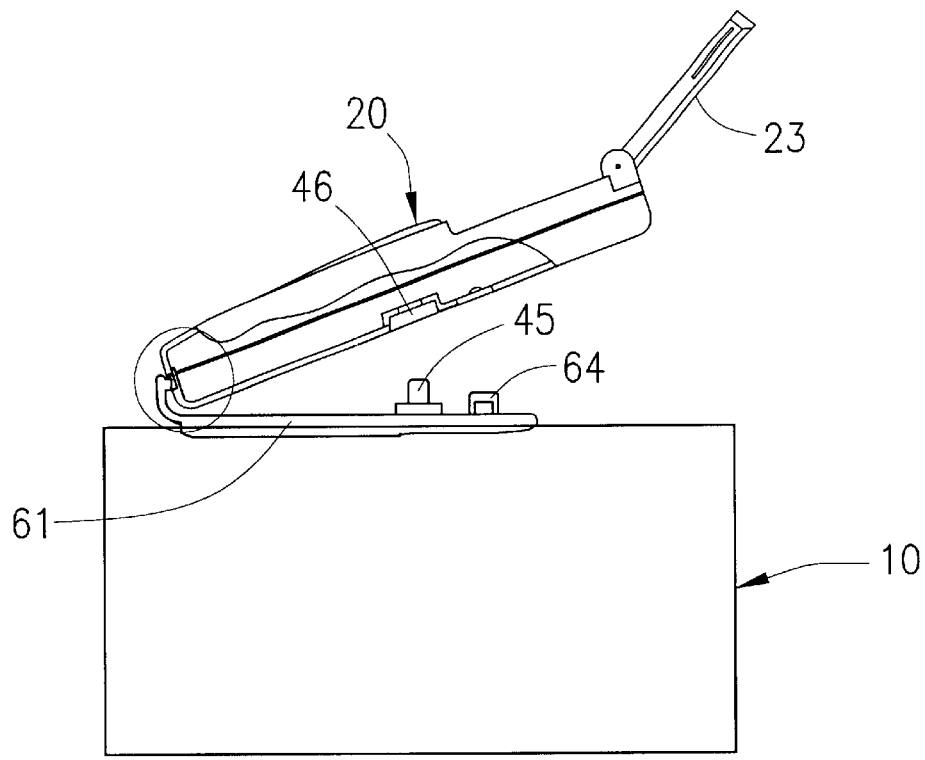
FIG. 13 shows at (a) a partially broken side view of the main body and the cuff for illustrating the mounting method subsequent to FIG. 12, and at (b) an enlargement view of a circled portion of FIG. 13 at (a)
Figure 13B:
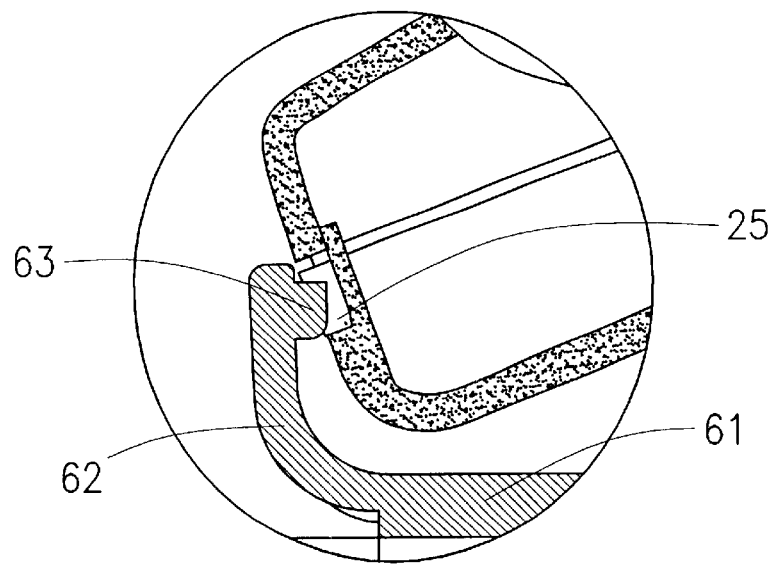
Figure 14A:
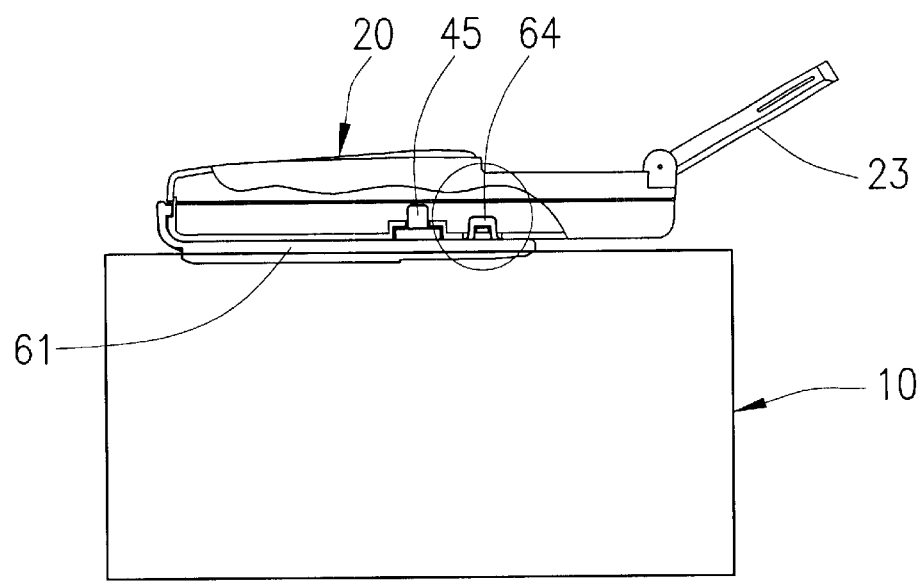
FIG. 14 shows at (a) a partially broken side view of the main body and the cuff for illustrating the mounting method subsequent to FIG. 13, and at (b) an enlargement view of a circled portion of FIG. 13 at (a)
Figure 14B:
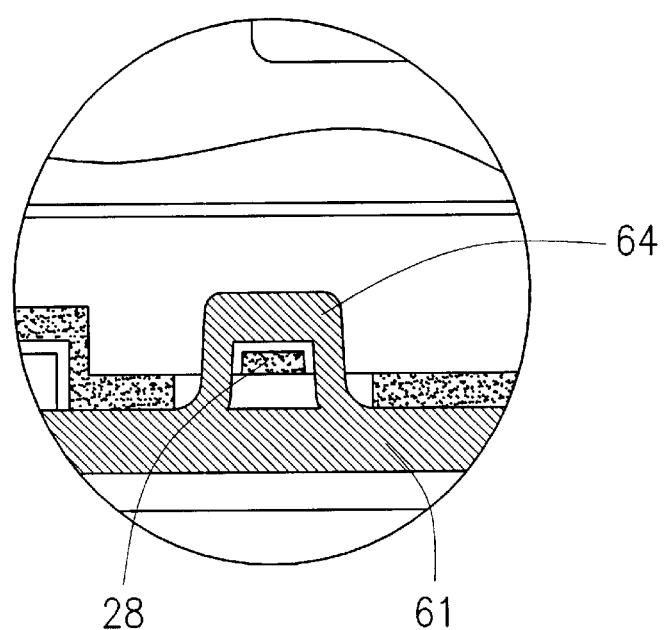

Referring to FIGS. 12 to 14, a mounting method for mounting the main body 20 on the cuff 10 will be described hereinafter. First, as shown in FIG. 12 showing at (a) a partially broken side view of the main body of FIG. 8 and the cuff of FIG. 11, and at (b) an enlargement view of a circled portion of FIG. 12 at (a), the projection 63 of the base 61 of the cuff 10 is opposed to the groove 25 of the main body 20, and is hooked by the groove 25 as shown in FIG. 13. As the main body 20 is pushed against the cuff 10, the projection 63 is brought to be engaged with the groove 25 and the nail receiver 54 enters into the opening 27 of the main body 20 to be engaged with the nail 28 as shown in FIG. 14, whereby the main body 20 is fixed to the cuff 10. In this state the air connection mouth 45 of the cuff 10 is engaged with the air connection mouth 46 of the main body 20, so that the connection mouths 45 and 46 are airtightly connected by the O-ring of the connection mouth 46. When the main body is required to be detached from the cuff 10, the nail 28 is detached from the nail receiver 64 by depressing the push button 26 of the main body 20, whereby the main body 20 is easily detached.

As described above, the air connection mouth 46 of the main body 20 is located at the position W/2 of the dimension W, the connection of the air connection mouths 45 and 46 is little affected to leak air by curve of a surface of the cuff 10 which is made when the cuff 10 is wound around the arm, in comparison with the design in which the air connection mouth 46 is located near end portion thereof. Moreover, the air connection mouth 45 of the cuff 10 is located at the position L/2 of the dimension L, the connection of the air connection mouths 45 and 46 is little affected to leak air by curve of a surface of the cuff 10 which is made when the cuff 10 is inflated by ventilation, in comparison with the design in which the air connection mouth 45 is located near end portion thereof. Thus, by both mutual effects, the air leaking at the connection may be effectively prevented.

Figure 15:
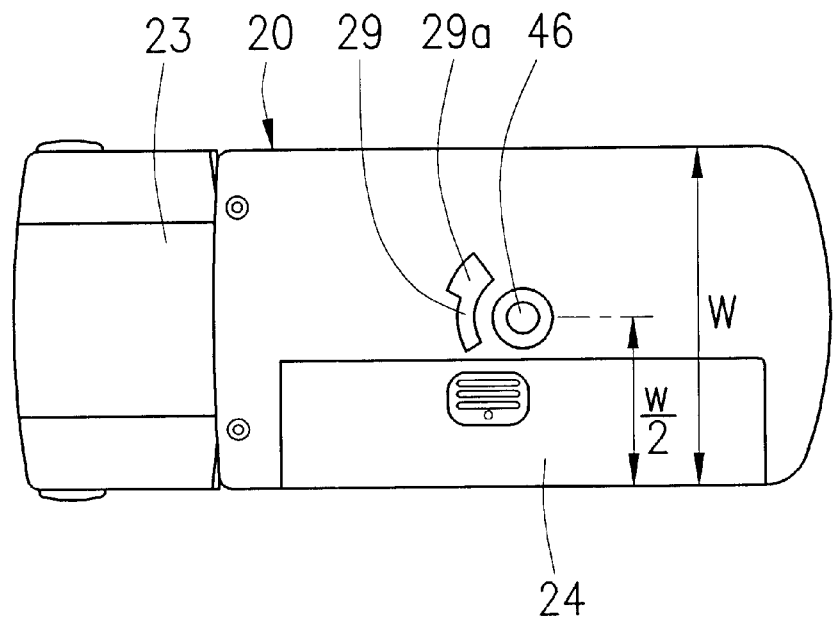
FIG. 15 is a bottom view of a main body to illustrate another mounting state of the main body to be mounted on a cuff.
Figure 16A:
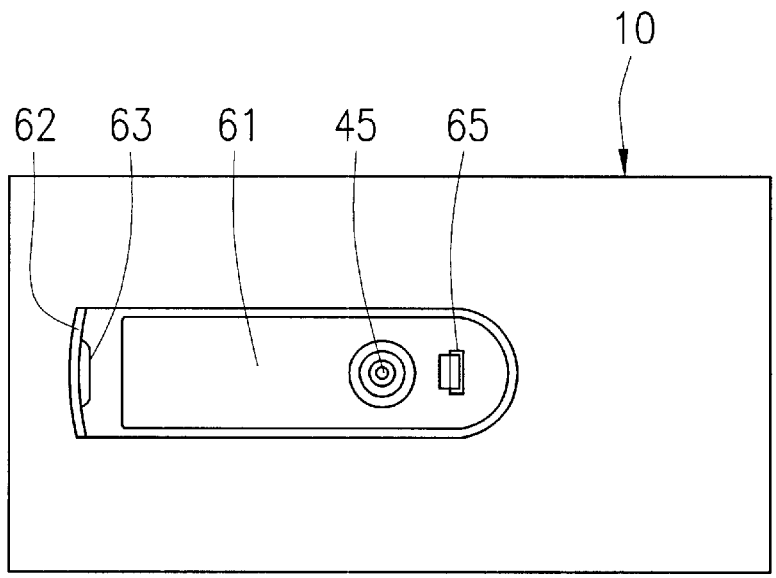
FIG. 16 shows at (a) a top view of the cuff to be mounted by the main body of FIG. 15, and at (b) a side view of the cuff.
Figure 16B:
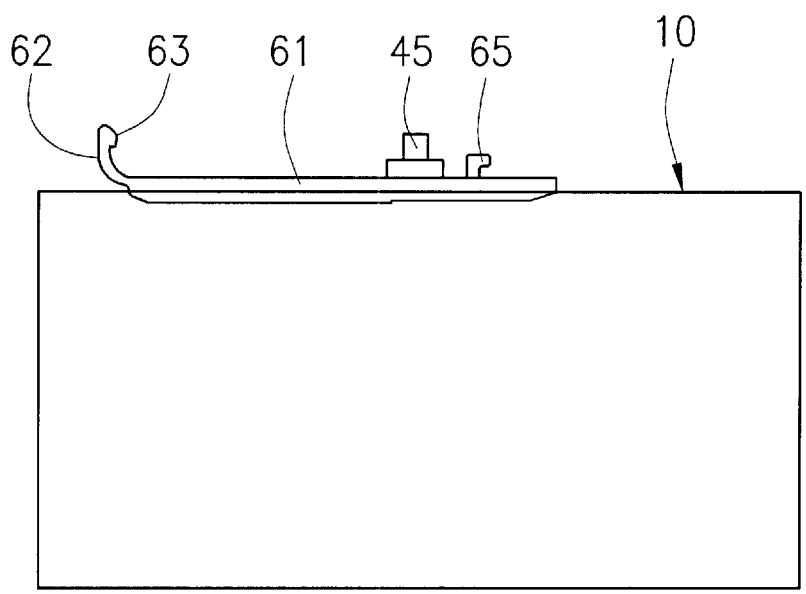

Referring to FIGS. 15 and 16, a different mounting method from the above-described blood pressure monitor will be described hereinafter. In FIG. 15 there is shown a bottom wall view of a main body 20, and same components are represented by the same reference numbers. On the bottom wall of the main body 20 there is disposed an arc-shaped hook engagement opening (projection receiving opening) 29 provided with an enlarged portion 29a having a wider opening. FIG. 16 shows at (a) a top view of the cuff 10 and at (b) a side view of the cuff 10, and same components are represented by the same reference numbers as well. In this cuff 10, an L-shaped hook (projection) 65 is disposed on a base 61, instead of the above-mentioned nail receiver 64.

Figure 17A:
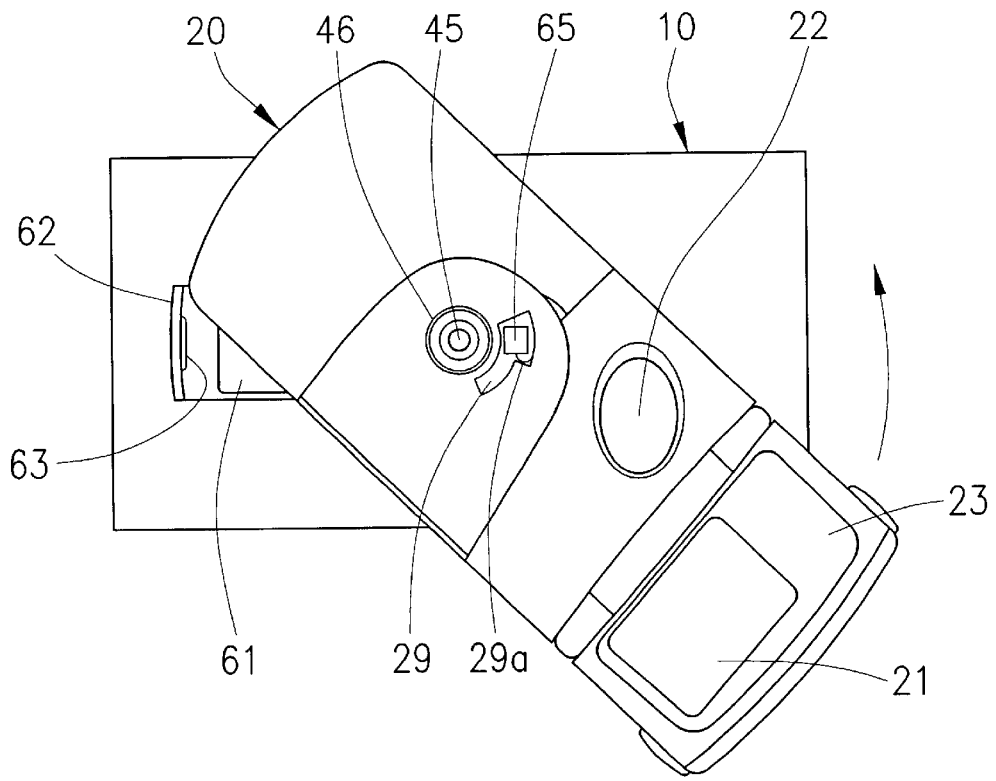
FIG. 17 shows at (a) a partially transparent top view of the main body of FIG. 15 to be mounted on the cuff of FIG. 16 to illustrate an initial mounting state, and at (b) a partially transparent top view of the same to illustrate a complete mounting state.
Figure 17B:
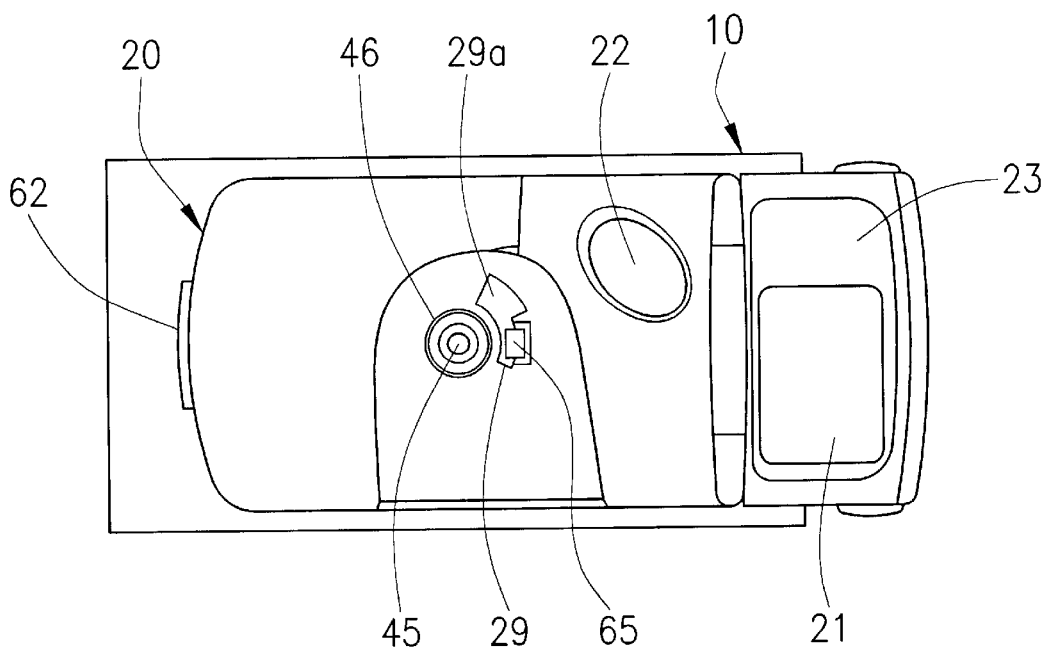
Figure 18A:
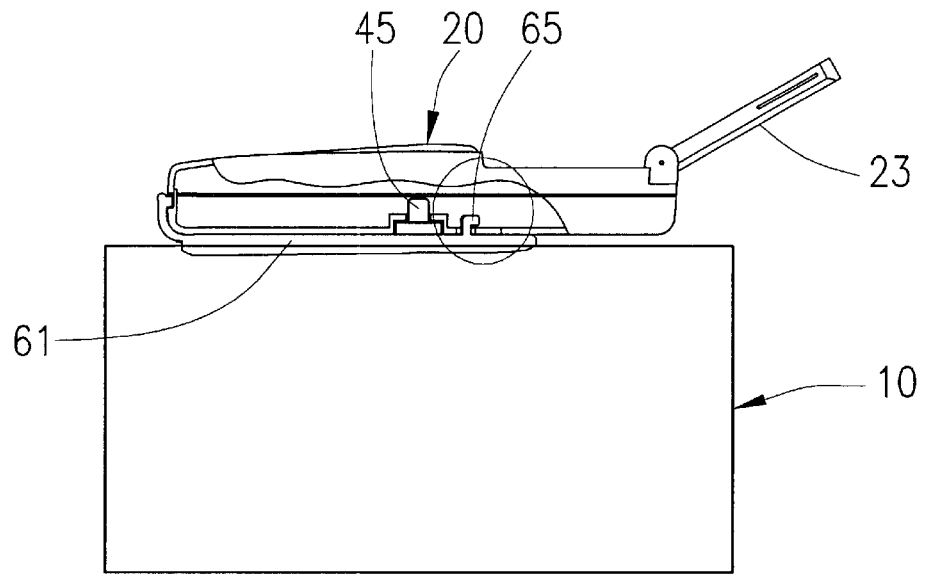
FIG. 18 shows at (a) a side view of FIG. 17(*b*), and at (b) an enlargement view of a circled portion of FIG. 18(*a*)
Figure 18B:
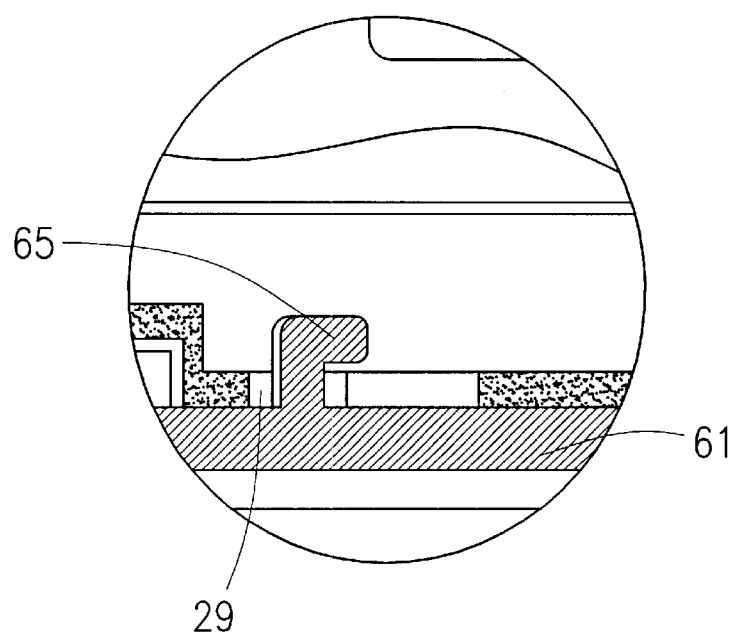
Figure 19A:
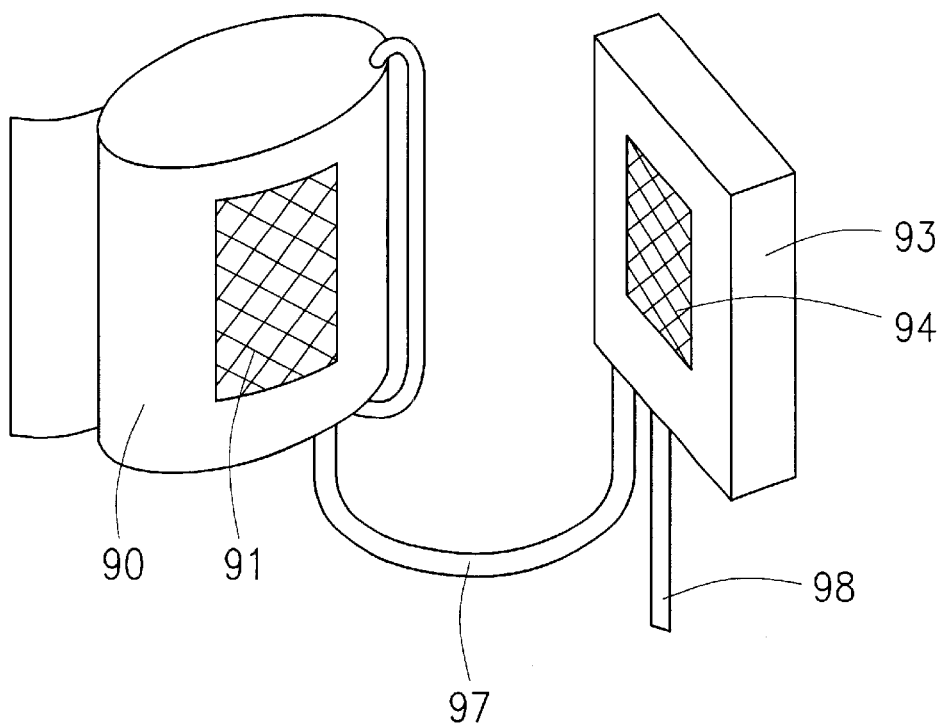
FIG. 19 shows conventional blood pressure monitors wherein main bodies are adapted to be detachably mounted on cuffs.
Figure 19B:
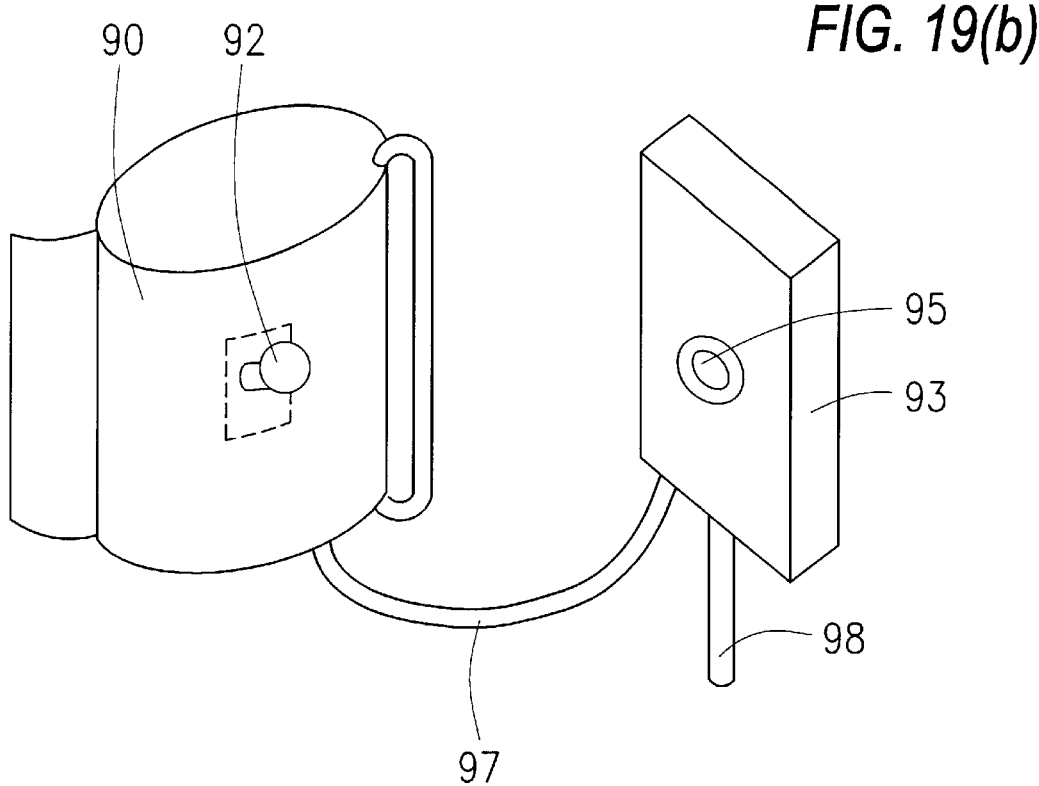

Referring to FIG. 17 which shows at (a) a partially transparent top view of the main body 20 to illustrate an initial mounting state, and at (b) a partially transparent top view of the same to illustrate a complete mounting state and FIG. 18 which shows at (a) a side view of FIG. 17(b) and at (b) an enlargement view of a circled portion of FIG. 18(a). First, in FIG. 17 at (a), the hook 65 of the base 61 is inserted into the enlargement portion 29a of the hook engagement opening 29 of the main body 20, wherein an air connection mouth 45 of the base 61 is entered into an air connection mouth 46 of the main body 20 and the connection mouths 45 and 46 are jointed. As the main body 20 is turned in an arrow marked direction, the hook 65 reaches to an opposite side of the hook engagement opening 29 to overlap with an edge of the hook engagement opening 29, and a convex portion 63 of the base 61 comes into engagement with a groove 25 (FIG. 8) of the main body 20 (FIG. 17(b) and FIG. 18(a) and (b)). Thus, the main body 20 is fixed to the cuff 10. When the main body 20 is detached from the hook 10, the main body 20 is turned in a counter direction of the arrow mark, whereby the hook 65 reaches to the enlargement portion 29a of the hook engagement opening 29. Thus, the main body may be easily detached.

In the foregoing blood pressure monitors of FIGS. 8 to 18, the air connection mouths 45 and 46 may be jointed by the air tube of FIG. 7, in addition to such a construction that the main body 20 is mounted on the cuff 10.

What is claimed is:

1. A blood pressure monitor comprising:
   a cuff to be worn on a living body portion provided with an air component within said cuff for inflating and deflating said cuff, and
   a main body detachably mounted on said cuff and provided with an electrical component, said main body being capable of functioning as part of the blood pressure monitor when mounted on a separated away from the cuff;
   said main body being electrically connected with said cuff by wires or by a wireless connection.

2. A blood pressure monitor comprising:
   a cuff to be worn on a living body portion;
   a main body detachably mounted on said cuff provided with an air component for inflating and deflating said cuff and being capable of functioning as a part of the blood pressure monitor mounted on and separated away from the cuff;
   a connecting air tube; and
   air connection openings disposed on said cuff and main body;
   wherein the air connection openings are directly connected without said connecting air tube when the main body is mounted on the cuff for blood pressure monitoring, and the air connection openings are indirectly connected by the connecting air tube when the cuff is placed away from the cuff for blood pressure monitoring.

3. A blood pressure monitor according to claim 2, wherein the air connection opening of said cuff is disposed on a main body mounting portion of said cuff, and the air opening of said main body is disposed on a rear wall of said main body corresponding to said air connection opening of said cuff.

4. A blood pressure monitor according to claim 3, further comprising a projection disposed on the main body mounting portion of said cuff and a projection receiving portion disposed on the rear wall of said main body.

5. A blood pressure monitor according to claim 3, wherein an engagement portion is disposed on one of said main body mounting portion of the cuff and said rear wall of the main body and an engagement receiving portion is disposed on other one thereof to be detachably engaged with said engagement portion while a projection is disposed on one of said main body mounting portion of the cuff and said rear wall of the main body and a projection receiving portion is disposed on other one thereof to be detachably engaged with said projection, in which said projection is engaged with said projection receiving portion for mounting said main body to said cuff after said engagement portion is engaged with said engagement receiving portion so that said main body may be secured to said cuff.

6. A blood pressure monitor according to claim 3, wherein a projection is disposed on one of said main body mounting portion of the cuff and said rear wall of the main body and a projection receiving opening is disposed on other one thereof to be detachably engaged with said projection, in which said projection is inserted into said projection receiving opening and said main body is rotated for mounting said main body to said cuff so that said main body may be secured to said cuff.

7. A blood pressure monitor according to claim 3, wherein said main body mounting portion of said cuff is provided with a base for detachably supporting said main body such that said air connection openings are connected when said main body is mounted on said base.

8. A blood pressure monitor according to claim 2, wherein the air connection opening of said main body is located at about a center of said main body in a longitudinal direction of said cuff when said main body is mounted on said cuff.

9. A blood pressure monitor according to claim 2, wherein the air connection opening of said cuff is located at about a center of said cuff in a width direction of said cuff.

* * * * *